United States Patent [19]

Blum et al.

[11] Patent Number: 4,624,947
[45] Date of Patent: Nov. 25, 1986

[54] 4-DIMETHYLAMINO-1-HYDROXYBUTANE-1,1-DIPHOSPHONIC ACID, SALTS THEREOF, AND PROCESSES THEREFOR

[75] Inventors: Helmut Blum, Duesseldorf; Siglinde Hemmann, Meerbusch, both of Fed. Rep. of Germany

[73] Assignee: Henkel Kommanditgesellschaft auf Aktien, Duesseldorf, Fed. Rep. of Germany

[21] Appl. No.: 776,337

[22] Filed: Sep. 16, 1985

[30] Foreign Application Priority Data

Sep. 21, 1984 [DE] Fed. Rep. of Germany ....... 3434667

[51] Int. Cl.$^4$ .................. C07F 9/38; A61K 31/045
[52] U.S. Cl. .................................. 514/108; 210/700; 252/8.8; 260/502.5 C
[58] Field of Search ................... 260/502.5 C; 514/108

[56] References Cited

U.S. PATENT DOCUMENTS

| | | | |
|---|---|---|---|
| 3,962,432 | 6/1976 | Schmidt-Dunker | 514/108 |
| 4,054,598 | 10/1977 | Blum et al. | 260/502.5 |
| 4,267,108 | 5/1981 | Blum et al. | 260/502.5 C |
| 4,304,734 | 12/1981 | Jary et al. | 260/502.5 C |
| 4,327,039 | 4/1982 | Blum et al. | 260/502.5 C |
| 4,407,761 | 10/1983 | Blum et al. | 260/502.5 C |

FOREIGN PATENT DOCUMENTS

| | | |
|---|---|---|
| 0039033 | 4/1981 | European Pat. Off. . |
| 2405254 | 3/1975 | Fed. Rep. of Germany . |
| 2096889 | 10/1982 | United Kingdom ............... 514/108 |

*Primary Examiner*—J. E. Evans
*Attorney, Agent, or Firm*—Ernest G. Szoke; Henry E. Millson, Jr.

[57] ABSTRACT

4-Dimethylamino-1-hydroxybutane-1,1-diphosphonic acid and water-soluble salts thereof, methods for their preparation, and uses thereof as complexing agents.

5 Claims, No Drawings

4-DIMETHYLAMINO-1-HYDROXYBUTANE-1,1-DIPHOSPHONIC ACID, SALTS THEREOF, AND PROCESSES THEREFOR

BACKGROUND OF THE INVENTION

1. Field of the Invention

This invention relates to 4-dimethylamino-1-hydroxybutane-1,1-diphosphonic acid (also referred to hereinafter as "DABD"), to water-soluble salts thereof, to a process for their production, and to their use.

2. Description of Relevant Art

German Pat. No. 2,534,391 describes 1-hydroxy-3-aminoalkane-1,1-diphosphonic acids, their production and their use as complexing agents for alkaline earth metal ions, preferably calcium ions. The use of these compounds for pharmaceutical purposes is also described.

German Pat. No. 2,405,254 describes the use of 3-amino-1-hydroxy-propane-1,1-diphosphoric acid or its water-soluble salts for influencing calcium metabolism disturbances in the animal body.

European Pat. No. 39,033 describes and improved process for the production of ω-amino-1-hydroxyalkylidene-1,1-bis-phosphonic acids.

DESCRIPTION OF THE INVENTION

Other than in the operating examples, or where otherwise indicated, all numbers expressing quantities of ingredients or reaction conditions used herein are to be understood as modified in all instances by the term "about".

The object of the present invention is to provide a new compound which shows improved complexing properties.

The new compound to which the present invention relates is 4-dimethylamino-1-hydroxybutane-1,1-diphosphonic acid corresponding to the following formula

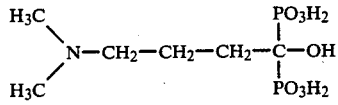

and its water-soluble salts. The invention also relates to a process for their production.

The invention further relates to the use of 4-dimethylamino-1-hydroxybutane-1,1-diphosphonic acid and water-soluble salts thereof for complexing divalent and polyvalent metal ions, especially alkaline earth metal ions, and more especially calcium ions.

DABD is produced by phosphonylation of 4-dimethylamino-butyric acid hydrochloride with phosphorous acid in the presence of phosphoryl chloride. DABD can also be produced by other known phosphonylation reactions (for example using $PCl_3$ etc.) or by the process of European Pat. No. 39,033.

The starting product used is normally 4-aminobutyric acid which is dialkylated by the method known from Houben-Weyl 11/2 after reducing methylation by Leuckart's method.

DABD and water-soluble salts thereof show outstanding complexing power with respect to divalent and polyvalent metal ions, such as for example Ca, Cu, Fe, Cr and others, at various temperatures and pH-values.

In particular, they show an especially good calcium binding power which is better than that of known analogous compounds, as is readily demonstrated by the Hampshire Test.

Accordingly, DABD and its water-soluble salts are useful as complexing agents and sequestrants.

In addition to their excellent complexing power, DABD and its water-soluble salts show strong threshold activity, i.e. they are capable of preventing the precipitation of difficulty soluble alkaline earth metal salts, even in inoculation quantities, i.e. substoichiometric quantities.

DABD and its water-soluble salts can be used as complexing agents for a variety of purposes. For example, they can be used in the softening of water where the threshold effect mentioned above plays a crucial part. Accordingly, there is no need to use stoichiometric quantities because precipitations of calcite are retarded to a considerable extent even with substoichiometric quantities.

They are also eminently suitable for use as corrosion and scaling inhibitors for cooling water, particularly in combination with known additives.

By virtue of the above-mentioned properties, DABD and its water-soluble salts can be used, for example, for softening fabrics in which alkaline earth metal salts have been deposited and for reducing the accumulation of ash in fabrics. They are also suitable for use as complexing builders in detergents and cleaners and can be used in combination with known anion-active, cation-active or nonionic wetting agents. They can also be used in combination with caustic alkalis, alkali carbonates, alkali silicates, phosphates or borates.

By virtue of their strong complexing power, they can also be used with advantage in systems in which heavy metal ions, for example copper ions, initiate undesirable effects, such as for example the decomposition of per compounds in bleaches and discoloration or rancidity in fats and soaps.

DABD and its water-soluble salts are also suitable for cleaning hard objects, such as metal or glass. In this connection, they can be used as an additive to bottle washing preparations.

The products of the invention are also suitable for pharmaceutical applications, more particularly for treating disturbances of the calcium and phosphate metabolism and associated illnesses in mammalian bodies. These diseases can be divided into two categories:

1. Abnormal depositions of difficulty soluble calcium salts, mostly calcium phosphate, causing bone malformations, pathological hardening of tissues, and secretions in organs.
2. The abnormal dissolution of hard tissues causing losses of hard bone substance, which cannot be replaced or are replaced only by incompletely crystallized tissue. This dissolution is frequently accompanied by pathologically high calcium and phosphate concentrations in the plasma.

These diseases include osteoporosis, osteodystrophy, Paget's disease, myositis ossificans, Bechterew's disease, cholelithiasis, nephrolithiasis, urinary calculus, hardening of the arteries(sclerosis), arthritis, bursitis, neuritis, and tetany.

In addition, DABD and its water-soluble salts can be used in cosmetic preparations, such as in particular toothpastes, mouthwashes and similar products, because they considerably reduce or inhibit the formation of tartar.

Suitable water-soluble salts of DABD are sodium potassium, ammonium and substituted ammonium salts, such as mono-, di- or triethanolammonium salts, and also hydrates thereof. Lithium salts can also be used. The sodium, potassium and ammonium salts and also dialkylammonium salts and triethanolamine salts are preferred. Mixtures of the salts can also be used.

For pharmaceutical applications, the dosage of the compounds used is variable and depends upon the particular conditions, such as the nature and gravity of the illness, the duration of the treatment and the particular compound. Individual daily doses can range from 0.05 to 500 mg per kg of bodyweight. The preferred daily dosage is 1 to 50 mg per kg of bodyweight, administered in up to 4 individual doses. The higher dosages are necessary for oral application due to limited resorption. In the event of prolonged treatment, relatively high initial dosages normally have to be followed up with smaller dosages to maintain the desired effect.

DABD and its salts may be applied both orally and also—in hypertonic solution—subcutaneously, intramuscularly or intravenously. The preferred dosage ranges for these applications in mammals are as follows (in mg/kg/day):

| oral | 1 to 50 |
|---|---|
| subcutaneous | 1 to 50 |
| intramuscular | 0.05 to 10 |
| intravenous | 0.05 to 2 |

The compounds can be formulated for administration in finished unit dosage forms, such as tablets, pills, capsules or in injection solutions, with pharmaceutical adjuvant materials. Pharmaceutical adjuvant materials for oral dosage forms include, for example, inert diluents, such as sodium carbonate, lactose, granulating and disintegrating agents, for example, maize starch or alginic acid; binding agents, for example, starch, gelatin or acacia; and lubricating agents, for example, stearic acid or talc. Pharmaceutically acceptable base addition salts are used for the above pharmaceutical applications. Such salts include the sodium, potassium, ammonium, and lower alkanol ammonium salts such as the mono-, di-, or tri-ethanolammonium salts.

For domestic animals, the compounds can also be used in feeds or as feed additives.

Finally, DABD and its salts are suitable for use as additives to preparations for the production of 99 m technetium radiodiagnostic preparations.

The invention is illustrated but not limited by the following Examples.

EXAMPLE 1

A mixture of 1 mole of phosphorous acid and 1 mole of phosphoryl chloride is prepared in an inert gas atmosphere, followed by the gradual addition of 0.5 mole of dimethyl-aminobutyric acid hydrochloride. The reaction mixture was heated to 100° C. and left at that temperature for 4 hours, during which time it thickened into a foam-like mass which could no longer be stirred. After cooling, 225 ml of water were added to the reaction product which was then thoroughly boiled for the purpose of complete hydrolysis. The hydrolyzate was filtered clear over active carbon, followed by addition of the same quantity by volume of methanol.

After standing for several hours, the crystalline 4-dimethylamino-1-hydroxybutane-1,1-diphosphonic acid precipitated was filtered off, washed with methanol and dried at 60° C.

Yield: 64%.

M.p.: 212° C.

a.w. by pH-titr.: Found: 279.8 (1st t.p.) 278.3 (2nd t.p.). Calculated: 277.

Elemental analysis:

| C | H | N | P |
|---|---|---|---|
| 25.8 | 6.29 | 4.96 | 22.2 |
| (25.99) | (6.14) | (5.05) | (22.38) |

EXAMPLE 2

0.1 mole of the aminodiphosphonic acid prepared in Example 1 were suspended in 125 ml of water and 10% sodium hydroxide added to the resulting suspension in the quantity calculated for the disodium salt. After neutralization, the pH-value of the solution was 8.3. Precipitation with a mixture of ethanol/methanol gave an oil which was solidified by further alcohol treatment. After drying over blue gel, a salt having a residual water content of approx. 10% was obtained. The disodium-4-dimethylamino-1-hydroxybutane-1, 1-diphosphonate was isolated in anhydrous form by drying at 110° C. over $P_2O_5$.

% C 22.3 (calc. 22.4), % H 4.51 (4.67), % P 19.1 (19.3), N 4.31 (4.36), Na 14.2 (14.3).

Atomic weight by potentiometric titration: 317.1 (calc. 321).

COMPARISON EXAMPLE 1

The complexing properties of DABD were determined by the Hampshire Test. The comlexing properties of similar known compounds were also determined for comparison. The results are shown in Table I below.

TABLE I

| | Complexing agent | mg of $CaCO_3$/g of acid, pH 11 |
|---|---|---|
| A | $Me_2N(CH_2)_3C(OH)(PO_3H_2)_2$ | >5000 |
| B | $H_2N(CH_2)_3C(OH)(PO_3H_2)_2$ | 600 |
| C | $CH_3CH(NH_2)CH_2C(OH)(PO_3H_2)_2$ | 710 |
| D | $H_2N(CH_2)_2C(OH)(PO_3H_2)_2$ | 470 |
| E | $Me_2N(CH_2)_2C(OH)(PO_3H_2)_2$ | >2500 |

A = according to the invention
B–E—comparison compounds

COMPARISON EXAMPLE 2

The threshold activity, i.e. the ability of the complexing agent to prevent or retard the scaling of difficulty soluble calcium salts (gypsum and calcite), in substoichiometric quantities, was tested in synthetic salt water which corresponds in composition to the low-salinity injection waters of mineral deposits.

The threshold activity of the diphosphonic acid of the invention was tested in the inoculation range of 1 to 20 ppm in the case of gypsum and 5 to 50 ppm in the case of calcite.

A calcium salt solution of 211° d was used in the gypsum inhibition test and one of 282° d, consisting of a mixed hardness of 231° d Ca and 51° d Mg hardness, in the calcite inhibition test. The test solutions were stored in a water bath for 3 days at 70° C. The quantity of alkaline earth salt remaining in solution was then determined.

Determination was carried out by standard test method 03-74 of the National Association of Corrosion Engineers.

The threshold activity of similar known compounds was also determined for comparison. The results are shown in Tables II and III below.

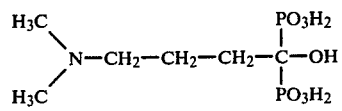

TABLE II

| | | Gypsum inhibition (5134 mg of CaSO$_4$/l) | | | | | |
|---|---|---|---|---|---|---|---|
| | | Quantity of calcium sulfate remaining in solution in mg/l | | | | | |
| | Inhibitor | 1 ppm | 3 ppm | 5 ppm | 10 ppm | 20 ppm | Blank value |
| A | Me$_2$N(CH$_2$)$_3$C(OH)(PO$_3$H$_2$)$_2$ | 5012 | 5102 | 5090 | 5140 | 5104 | 3473 |
| B | H$_2$N(CH$_2$)$_3$C(OH)(PO$_3$H$_2$)$_2$ | 3744 | 3812 | 3800 | 3974 | 4220 | 3460 |
| C | CH$_3$CH(NH$_2$)CH$_2$C(OH)(PO$_3$H$_2$)$_2$ | 3400 | 3482 | 3700 | 3824 | 4190 | 3617 |
| D | H$_2$N(CH$_2$)$_2$C(OH)(PO$_3$H$_2$)$_2$ | 3498 | 3526 | 3554 | 3800 | 4010 | 3512 |
| E | Me$_2$N(CH$_2$)$_2$C(OH)(PO$_3$H$_2$)$_2$ | 3583 | 3738 | 3918 | 4296 | 5012 | 3492 |

A = according to the invention
B–E = comparison compounds

TABLE III

| | | Calcite inhibition (4133 mg of CaCO$_3$/l) | | | | |
|---|---|---|---|---|---|---|
| | | Quantity of calcium carbonate remaining in solution in mg/l | | | | |
| | Inhibitor | 5 ppm | 10 ppm | 20 ppm | 40 ppm | Blank value |
| A | Me$_2$N(CH$_2$)$_3$C(OH)(PO$_3$H$_2$)$_2$ | 4020 | 4092 | 4140 | 4101 | 2360 |
| B | H$_2$N(CH$_2$)$_3$C(OH)(PO$_3$H$_2$)$_2$ | 2814 | 2966 | 3044 | 3408 | 2400 |
| C | CH$_3$CH(NH$_2$)CH$_2$C(OH)(PO$_3$H$_2$)$_2$ | 3222 | 3200 | 3412 | 3490 | 2375 |
| D | H$_2$N(CH$_2$)$_2$C(OH)(PO$_3$H$_2$)$_2$ | 2664 | 2612 | 2878 | 3010 | 2430 |
| E | Me$_2$N(CH$_2$)$_2$C(OH)(PO$_3$H$_2$)$_2$ | 3657 | 3692 | 3980 | 3998 | 2440 |

A = according to the invention
B–E = comparison compounds

Comparison of DABD, the compound of the invention, with the comparison compounds B to E shows that DABD has a far greater complexing power and considerably better threshold activity. As can be seen from Table II for example, almost complete inhibition is obtained by comparison with the blank value where DABD is used in a quantity of only 1 ppm, whereas with the comparison compounds perceptible inhibition is only obtained with quantities of 20 ppm and greater. Similar results are also apparent from Table III.

It can be concluded therefore that DABD shows surprisingly greater complexing power and improved threshold activity compared to those of similar and analogous known compounds. This could not in any way be foreseen by those skilled in this art.

What is claimed is:

1. 4-Dimethylamino-1-hydroxybutane-1,1-diphosphonic acid of the formula and water-soluble salts thereof.

2. A pharmaceutical composition comprising a calcium binding effective quantity of 4-dimethylamino-1-hydroxybutane-1,1-diphosphonic acid or a pharmaceutically acceptable water-soluble base addition salt thereof, and pharmaceutical adjuvant material.

3. A pharmaceutical composition in accordance with claim 2 wherein said composition is in unit dosage form.

4. A method of treating a mammal requiring a calcium binding agent comprising treating said mammal with an effective quantity of 4-dimethylamino-1-hydroxybutane-1,1-diphosphonic acid or a pharmaceutically acceptable water-soluble base addition salt thereof.

5. A method in accordance with claim 4 wherein the effective quantity is in the range of from about 0.05 to about 500 mg. per kg. body weight.

* * * * *